Figure 1:
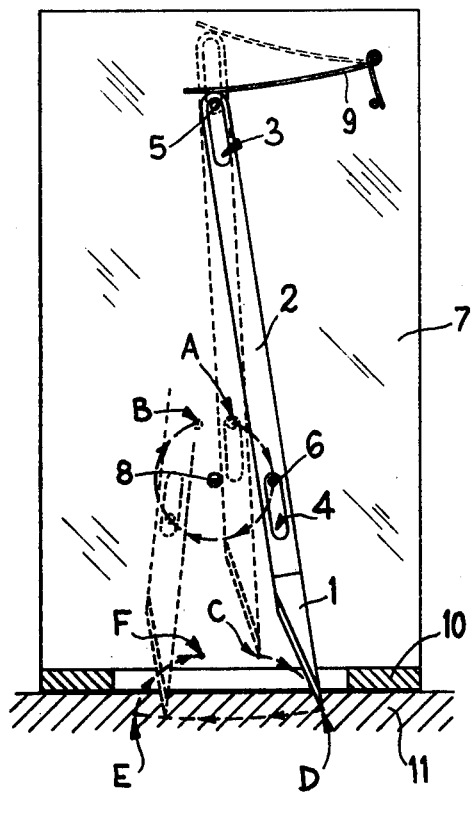

United States Patent [19]

Maiorano et al.

[11] 4,157,086
[45] Jun. 5, 1979

[54] APPARATUS FOR PROVIDING SKIN CUTS TO A PREDETERMINED MEASURE

[75] Inventors: Michele Maiorano; Luigi Valentini; Claudio Praga, all of Milan, Italy

[73] Assignee: Farmitalia Carlo Erba S.p.A., Milan, Italy

[21] Appl. No.: 865,398

[22] Filed: Dec. 29, 1977

Related U.S. Application Data

[63] Continuation of Ser. No. 657,935, Feb. 13, 1976, abandoned.

[30] Foreign Application Priority Data

Oct. 13, 1975 [IT] Italy ............................... 28218 A/75

[51] Int. Cl.² ............................................. A61B 17/32
[52] U.S. Cl. .................................... 128/637; 128/314
[58] Field of Search .............. 128/314, 2 G, 2 R, 305; 30/272 R

[56] References Cited

U.S. PATENT DOCUMENTS

| 6,240 | 5/1849 | Ives | 128/314 |
|---|---|---|---|
| 2,823,677 | 2/1958 | Hein | 128/314 |
| 3,760,809 | 9/1973 | Campbell | 128/314 |
| 3,902,475 | 9/1975 | Begg et al. | 128/2 G X |

Primary Examiner—Robert W. Michell
Assistant Examiner—Michael H. Thaler
Attorney, Agent, or Firm—Oblon, Fisher, Spivak, McClelland & Maier

[57] ABSTRACT

Improved apparatus for providing skin cuts to a predetermined measure in order to determine blood bleeding time, comprising a casing having a cutting blade accommodated therein and restrained to the casing through a pin coupling within an elongate groove. The blade is moved by a rotating spring member to cause its cutting end to project from a casing slit to a degree and travel that are exactly predetermined and repeatable.

4 Claims, 7 Drawing Figures

APPARATUS FOR PROVIDING SKIN CUTS TO A PREDETERMINED MEASURE

This is a continuation of application Ser. No. 657,935, filed Feb. 13, 1976, now abandoned.

This invention relates to an improved apparatus for providing skin cuts to a predetermined measure for determining bleeding time or the like.

It is well known that bleeding time is a test for evaluating platelet capability of normally operating in the early stages of physiological haemostasis.

The basic factors affecting such stages are the number and function of the platelets. In clinical medicine various pathological conditions are known as accompanying a thrombocytepeny or a thrombocytepathy, such pathological conditions being in part acquisitive and in part constitutional. Although altered in thrombocytepenies, said bleeding time is an effective diagnostic aid in said thrombocytepathies, since in the former case the platelet count is already of use for characterizing the pathological situation.

The pathological conditions accompanying an extension in bleeding time are as follows:

Thrombocytepeny (a) Idiopathic thrombocytepeny (I.T.P.)
(b) Acquisitive thrombocytepeny Thrombocytepathy Glanzmann's disease
Willebrand's disease
Paraproteinemias
Uremic syndromes
Salicylism (salicylic poisoning)

In the recent years the interest in platelets was aroused also in connection with possible relations thereof with thrombosis pathogenesis.

Thus, it appears that, as far as haemorrhage is concerned, the early stages leading to physiological haemostasis are the same as those being involved in developing the early or first plate-thrombuses which, then increasing through mechanisms involving haematic coagulation would lead to closure of arterious vessels or development of atheromas.

Some medicines or drugs (such as aspirin) proved to be capable of interferring with plate-function, and accordingly the clinical use thereof as antithrombotics has been suggested. Also in this case, bleeding time is an efficient test for treatment control, since any extensione thereof within determined limits is a sign that the medecine or drug activity is clinically acceptable, whereas an undue extension thereof would expose to a risk of a haemorrhagic diathesis.

Hitherto, clinical utility of bleeding time has been handicapped because of difficulty in test standardization.

Duke W. W. ("The relation of blood platelets to haemorrhagic disease", J.A.M.A., 55: 1185, 1910) was first in evaluating bleeding time through a small cut or incision to the ear lobe.

Ivy A. C. et al. ("The standardization of certain factors in the cutaneous "venostasis" bleeding time technique", J.Lab. Clin. Med., 26: 1812, 1941) increased the test sensitivity by pricking the volar surface of the forearm and applying a back pressure of 40 mm Hg to the damaged vessels.

Borchgrevink et al. ("The secondary bleeding time. A new method for the differentiation of haemorrhagic disease", Acta Medica Scand. 162: 361, 1958) modified Ivy's technique by replacing pricking or injection with a cut or incision by means of a lancet blade.

However, with all of these modifications, the haemorrhage time is scarcely reproducible in a same man due to difficulty in reproducing the cut depth.

Mielke et al. (Blodd 34, 2, 1969) provided a system including a blade-holder and a plastic guide enabling to obtain cuts of constant size and sufficiently reproducible.

However, Mielke's system has some disadvantages:

(a) time consuming and difficulty in sterilizingly inserting the blade into its associated blade-holder;
(b) necessity of suitably training the staff which has to carry out the test that can be highly affected by the operator's inexperience and lack of safety.

It is the primary object of the present invention to provide an improved apparatus for providing skin cuts to a predetermined measure in order to determine blood bleeding time, which apparatus ensures a remarkable accuracy in carrying out the cuts, causing the cutting blade to accurately follow a predetermined path.

It is another object of the invention to provide an apparatus of the above design, which is very strong, wear resistant and ensures a complete observance of sterility conditions.

These and still other objects are achieved by an apparatus comprising a casing accomodating a movable blade between two end of stroke positions through and respectively against the action of a spring, a manually operable member to move the blade to that end of stroke position where said spring is loaded, and a manually releasable member for retaining the blade at such a position, the casing comprising a slit through which the blade end projects as it moves between the two end of stroke positions for effecting a cut or incision, the apparatus being characterized in that said blade is restrained at one distal end thereof from said slit to said casing by means of a coupling comprising a pin inserted into and movable within an elongated slot, the blade being urged to said slit by a spring and being restrained at an intermediate location along its length, by means of a coupling comprising a pin inserted into and movable within an extended groove, to a rotating member, two ends of stroke being provided, at which the free cutting end of the blade is far away from said slit, said rotating member being driven from a spring which can be loaded by a handle or knob.

Figure 2:
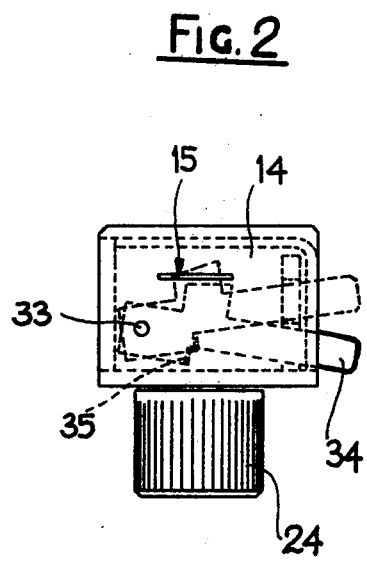
Figure 3:
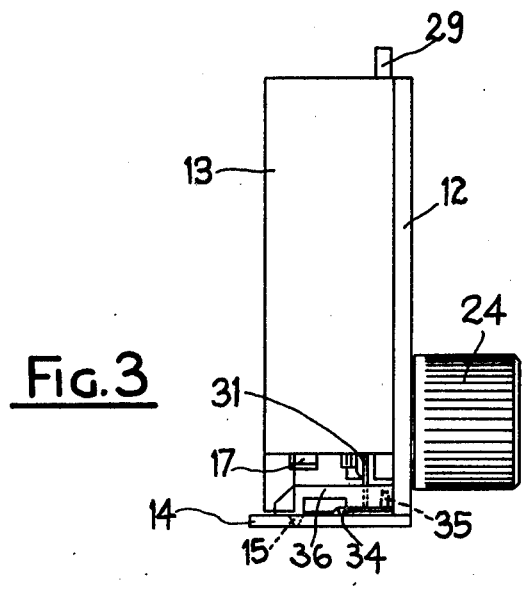
Figure 4:
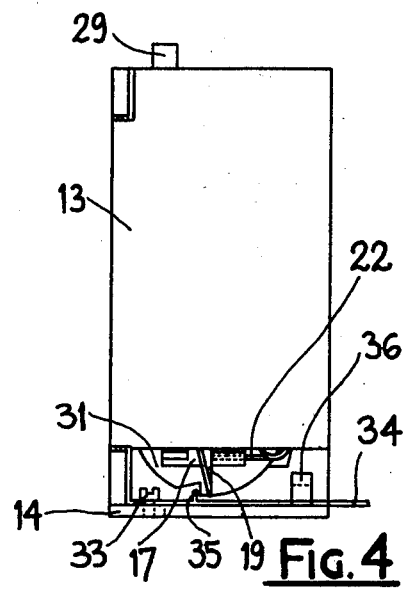
Figure 5:
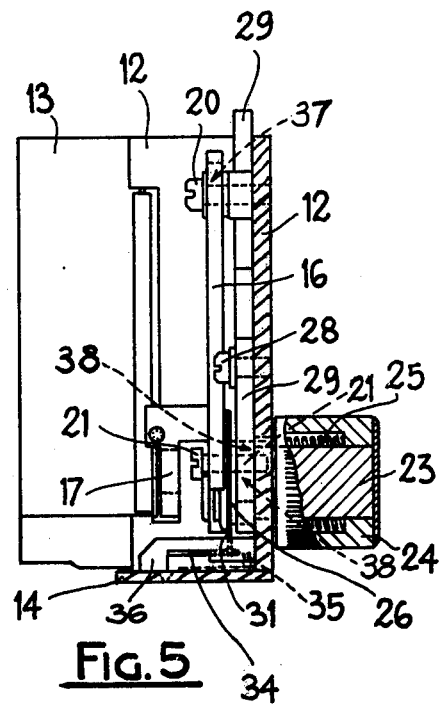
Figure 6:
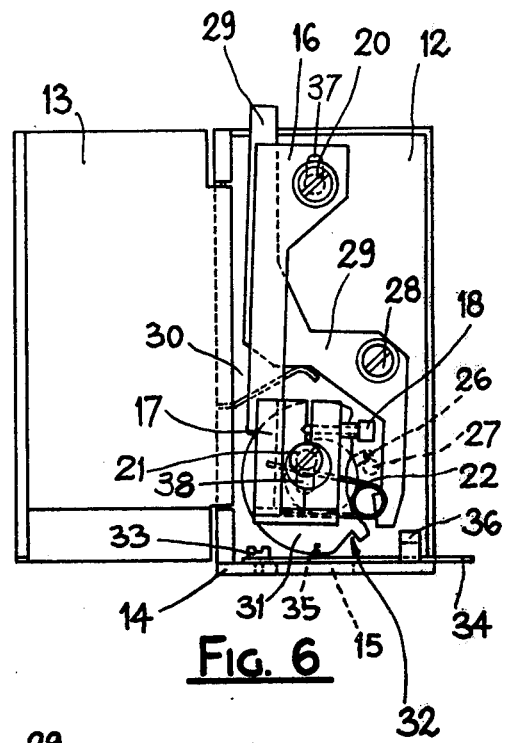
Figure 7:
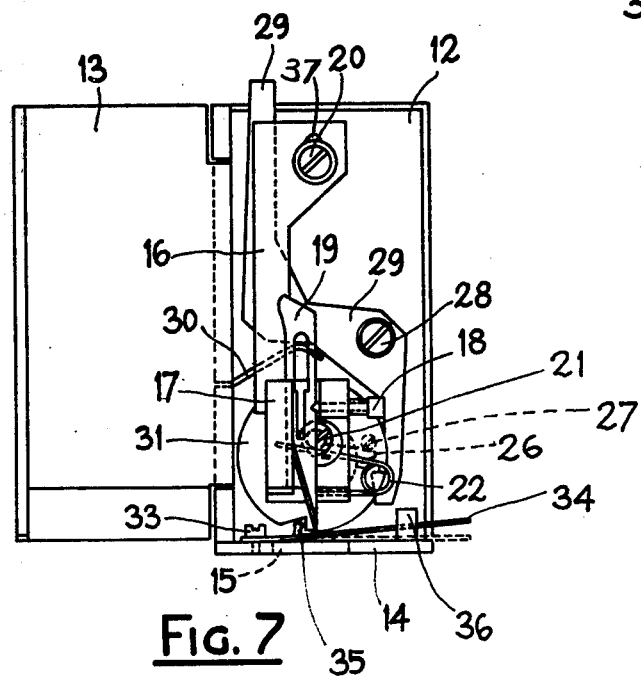

In order that the structure and features of the apparatus be more clearly understood, a preferred embodiment of the apparatus will now be described by mere way of unrestrictive example, reference being had to the accompanying drawings in which:

FIG. 1 is a view showing a schematic embodiment of the apparatus according to the invention;

FIGS. 2, 3 and 4 are bottom, side and front views, respectively, of the apparatus according to a practical embodiment; and FIGS. 5, 6 and 7 show the apparatus with the casing partly cut away in FIG. 5 and in side and front views in FIGS. 6 and 7, with the apparatus lid at open position for displaying the inner mechanical parts.

Referring first to FIG. 1, a schematic embodiment of the apparatus is shown therein. In such an embodiment, a lancet blade 1 is secured to one end of a movable arm 2, having two grooves 3 and 4, respectovely, formed therein, in which grooves two pins 5 and 6 are respectively inserted and movable, the pins guiding said movable arm 2. The upper pin 5 is directly secured to the apparatus casing 7, while the lower pin 6 is carried on a rotable bearing (not shown) and describes a circle having its center at 8.

Finally, a spring 9 is provided and acts on said arm 2 by downward urging it, that is towards a base wall 10 of the apparatus, in which wall a slit is formed, so that blade 1 projects therethrough during the apparatus operation for cutting the skin 11, on which said base 10 is bearing.

In operation, pin 6 will rotate about location 8 moving from the position indicated by letter A to the position indicated by letter B and causing the tip of blade 1 to move from the position indicated by letter C to the position indicated by letter D (in this movement step, the blade is lowered), then from said position D to the position indicated by letter E (in this movement step, arm 2 is retained by pin 5 and rotates through a small angle thereabout), and finally from said position E to the position indicated by letter F (in this movement step, the blade is raised and re-enters above base plate 10).

As a result, it can be readily understood that in its movement the blade has effected a cut or incision in the cutaneous tissue 11, of which cut or incision the size or measure can be time by time reproduced.

Referring now to FIGS. 2-7, in these figures a practical embodiment of the apparatus simply outlined in FIG. 1 is shown. This apparatus comprises a casing 12 provided with a lid 13, the bottom of which is transparent, and which is shown at closed position in FIGS. 2, 3 and 4 and at open position in FIGS. 5, 6 and 7, the casing comprising a base or bottom wall 14 having a slit 15 formed therein for the projection therethrough of the cutting blade end during the apparatus operation, said base or bottom wall 14 being preferably transparent.

As particularly shown in FIGS. 5-7, a movable arm 16 is accomodated within the casing and has integral therewith a bladeholder 17 provided with a screw 18 for securing a lancet blade 19, the latter being shown in FIG. 7 and not in FIG. 6.

At the top of arm 16 and in said bladeholder 17 two grooves 37 and 38 are formed, having inserted and movable therein an upper pin 20, secured to casing 12 for slot 37, and a lower movable pin 21 for groove 38, respectively, between said casing and bladeholder a spring 22 being effective to urge the bladeholder to said base or bottom wall 14.

A spindle 23 (FIG. 5) is freely rotably carried on casing 12 and on its side externally of the casing a handle or knob 24 is mounted and covers a spring 25, the latter reacting between said casing and spindle 23.

Inside of said casing 12, a snap pawl 26 radially projects from spindle 23 and interferes with a setscrew 27 fixed to the casing and serving as an abutment to limit travel of the snap pawl 26, and thereby determining the two ends of stroke for the blade movement, as shown in FIGS. 6 and 7 respectively. On other terms, after loading spring 25 by acting upon handle or knob 24 and considering to start from the end of stroke position shown in FIG. 7, said spring causes spindle 23 to rotate until pawl 26 comes against screw 27 at the position shown in FIG. 6.

Then, a snap lever 29 is mounted on a pin 28 integral with casing 12, of which lever 29 one end projects from the casing and is manually operable, while the other end has a detent for hooking and retaining pawl 26 at rest or inoperative conditions, when said pawl 26 is at the end of stroke position shown in FIG. 7. A return spring 30 is effective on lever 29 and tends to maintain the latter at the clamping position shown in FIG. 7.

Still on the portion of spindle 23 internally of the casing, a safety disc 31 is also mounted and has a notch 32, as clearly shown in FIGS. 4, 6 and 7.

Finally, it should be noted that a calibrating plate 34 is rockingly mounted on said base or bottom wall 14 and laterally thereof a small tooth 35 upwardly projects, a guide bridge 36 being provided above said plate 34, below which bridge said plate can swing between a position, at which it conceals the slit 15 of the base or bottom wall 14, and a position at which it clears said slit.

In order to use the apparatus, the following operations have to be carried out. First, spring 25 is loaded by clockwise rotating handle or knob 24 until pad 26 stops against screw 27 at the position shown in FIGS. 4, 5 and 7. Then, lid 13 is opened and calibrating plate 34 is displaced to the position shown in full lines in FIGS. 5 and 7 and in broken lines in FIG. 2, at which position said plate covers or conceals slit 15. It should be noted that this displacement or movement can be effected only when the apparatus is loaded, since under such conditions said notch 32 of safety disc 31 enables tooth 35 of plate 34 to be moved on one side of disc 31 (FIG. 6) until it is exactly positioned at said notch, thereby preventing any rotation (and accordingly any movement of the cutting blade) as far as said plate 34 is at the calibrating position above described. Under these conditions, that is plate covering slit 15, a new blade 1 is inserted into bladeholder 17, taking care that it will bottom said plate 34. The blade is then fastened by means of screw 18 and plate 34 is then moved back to the rest position shown by full lines in FIGS. 2, 4 and 6 and by broken lines in FIG. 7, and finally lid 13 is closed.

The transparent base or bottom wall 14 is brought to bear on the cutaneous tissue and the cut or incision is made by pressing the outer end of snap lever 29; thus, the detent of said snap lever will release pawl 26, which will rotate moving against setscrew 27, that is moving to the position shown in FIG. 6. As this movement occurs, also disc 31 will rotate through the same angle of rotation as pawl 26 and blade 1 will follow a path just as that described in connection with FIG. 1.

On opening lid 13, screw 18 can be unloosed and blade 1 can be removed or replaced.

It is important to note that the calibrating system comprising said plate 34 affords to use ordinary blades as those commercially available, and it is apparent that the apparatus could be simplified, as to its structure, should blades of a particular structural design be used.

As above stated, the path followed by the blade during cutting operation is curved, but shifting from a straight line is quite moderate. In any case, a perfectly rectilinear cut or incision can be made by making the outer surface of base or bottom wall 14 curved with its center at pin 20.

The above described apparatus enables to provide cutaneous cuts or incisions, all of which to a same size or measure, is of easy and ready use, since its operation only requires a pressure of one finger on the snap lever, it ensures a thorough observance of sterility conditions owing to the simplicity of setting up operations, and enables to obtain homogeneous on like results not depending on the operator, since cut or incision is automatically provided and can be carried out by any person without requiring any specific training.

It is apparent that cut or incision size would depend on the size of some parts comprising the apparatus and such cuts or incisions as those proposed by Mielke, that is 9 mm long and 1 mm deep, can be readily obtained.

What we claim is:

1. An apparatus for providing cutaneous or skin cuts to a predetermined measure, comprising:

a casing having a bottom plate and slit formed in said bottom plate;

a manually operable member exterior to the casing and coupled thereto, a first spring coupling said manually operable member to said casing;

a movable rigid assembly coupled to said casing, said assembly comprising an arm having an elongated slot at a distal end thereof relative to said bottom plate and an elongated groove intermediate between said slot and the other end of said arm, a bladeholder mounted on said arm, a blade with a cutting end coupled to said bladeholder, and a second spring for biasing said assembly such that said assembly is movable between two end of stroke positions at which said cutting end of said blade is farthest away from said bottom plate under and respectively against the action of said second spring;

means for coupling said assembly to said casing, said coupling means comprising a first pin integral with said casing inserted into and movable within said elongated slot of said arm of said rigid assembly, a rotatable member extending through said casing and coupled to said manually operable member, said rotatable member having a second pin integral therewith and inserted into and movable within said elongated groove of said arm such that said assembly and said shaft are loaded by said first spring, the assembly arm being urged towards said slit by said second spring and restrained at an intermediate location along its length by means of said second pin, said manually operable member provided for moving the assembly to that end of stroke position at which said first spring is loaded;

a manually releasable member for retaining the assembly at that end of stroke position at which said first spring is loaded;

whereby upon release of said manually releasable member rotational movement is transmitted to said rotatable member by said first spring, said rotatable member then acting on said arm by means of said second pin in said groove such that said cutting end of said blade defines a generally curvilinear trajectory through the casing at one side of said slit, followed by a relatively rectilinear movement to the other side of said slit, and then a curvilinear return trajectory to the interior of the casing, the end of said slot farther from said bottom plate contacting said first pin integral with the casing after the blade cutting end protrudes from said slit while allowing free movement of the second pin integral with the rotating member in said groove, the radial distance between said first pin contacting said end of said slot farther from said bottom plate and the cutting end of said blade defining a radius of curvature of said relatively rectilinear movement of said blade cutting end.

2. An apparatus according to claim 1, wherein a pawl is integral with said rotating member and bears on an abutment fixed to the casing to determine the two ends of stroke for the blade.

3. An apparatus according to claim 1, wherein said casing has a blade calibrating plate mounted thereon and movable between a position, at which it overlies said slit, and a position at which it is moved away from the slit.

4. An apparatus according to claim 3, wherein a tooth is integral with said calibrating plate and engages a notch of a disc integral with said movable member for preventing it from rotating under the conditions at which the plate is moved above said slit and the blade is at that end of stroke position at which said spring is loaded.

* * * * *